United States Patent [19]

O'Leary

[11] Patent Number: 5,780,527
[45] Date of Patent: Jul. 14, 1998

[54] PERFUMING DEVICE FOR PERFUMING AND SANITIZING AMBIENT AIR

[75] Inventor: Nicholas O'Leary, Slough, United Kingdom

[73] Assignee: Firmenich SA, Geneva, Switzerland

[21] Appl. No.: 624,463

[22] PCT Filed: Aug. 8, 1995

[86] PCT No.: PCT/IB95/00621

§ 371 Date: Apr. 3, 1996

§ 102(e) Date: Apr. 3, 1996

[87] PCT Pub. No.: WO96/05870

PCT Pub. Date: Feb. 29, 1996

[30] Foreign Application Priority Data

Aug. 19, 1994 [CH] Switzerland .................. 2561/94

[51] Int. Cl.⁶ .................................................. A61L 9/04
[52] U.S. Cl. .................................................. 523/102; 512/4
[58] Field of Search .................................. 512/4; 523/102

[56] References Cited

U.S. PATENT DOCUMENTS

| | | | |
|---|---|---|---|
| 4,136,250 | 1/1979 | Mueller | 528/29 |
| 4,160,754 | 7/1979 | Schapel | 523/102 |
| 4,362,841 | 12/1982 | Minatono et al. | 524/531 |
| 4,374,236 | 2/1983 | Znaiden | 523/102 |
| 4,587,129 | 5/1986 | Kliment | 523/100 |
| 4,722,865 | 2/1988 | Huizer | 424/417 |
| 4,961,871 | 10/1990 | Michael | 252/174.11 |
| 5,015,668 | 5/1991 | Ueda | 523/102 |
| 5,028,653 | 7/1991 | Desmonceau | 523/209 |
| 5,064,894 | 11/1991 | Desmonceau | 524/503 |
| 5,334,691 | 8/1994 | Gould | 424/409 |
| 5,569,683 | 10/1996 | Bootman | 523/102 |

FOREIGN PATENT DOCUMENTS

| | | |
|---|---|---|
| 0 023 084 A1 | 1/1981 | European Pat. Off. |
| 2 302 749 | 10/1976 | France . |
| 2 455 068 | 11/1980 | France . |

*Primary Examiner*—Paul R. Michl
*Attorney, Agent, or Firm*—Pennie & Edmonds LLP

[57] ABSTRACT

The device is useful for the perfuming, deodorising or sanitising of ambient air or enclosed spaces and comprises a gel element resulting from the in situ cross-linking of a functionalised liquid polymer, or a copolymer with a cross-linking agent, in the presence of a perfume, deodorising or sanitising base.

13 Claims, No Drawings

PERFUMING DEVICE FOR PERFUMING AND SANITIZING AMBIENT AIR

TECHNICAL FIELD

The present invention relates to perfumery and more particularly it concerns a perfuming device for purifying ambient air and enclosed spaces.

PRIOR ART

The utilisation of various devices for purifying ambient air has markedly increased in recent years. Air-deodorisers, for example, have henceforth become of current use in practically all households where they are used to mask bad odours as well as to impart ambient fragrances. The same applies to public places, e.g. offices or cars.

The solutions applied for the manufacture of this sort of devices are extremely varied. By way of example, one can mention here the systems based on the rapid diffusion of sanitising agents, which diffusion is promoted by the action of dispersing devices of spray type, aerosol or mechanical. Also known are solid devices consisting of elements impregnated with active sanitising ingredients, which elements are constituted by gels, such as agar-agar or sodium stearate gels, or by synthetic resin or mineral material blocks, e.g. plaster or silica. The prior art is also rich in examples wherein the deodorising devices are constituted by plastic packing elements enclosing the active ingredients in liquid form and wherein the diffusion of the sanitising vapours can take place through polymer semi-permeable walls. Finally, well-known are also the devices wherein the diffusion occurs by means of a wick put into contact, at one of its ends, with a sanitising liquid.

By experience, it is apparent that none of the existing systems can satisfy all the criteria of functionality and aesthetics required for a general use, some devices being more suitable for pulse perfuming of small or large spaces, others, on the contrary, more adapted for continuous sanitization.

Amongst the simple systems of proved efficacy one can find those based on the difflusion of sanitising agents wherein the support is constituted by a gelified material. They are devices which use in general the gelifying properties of carrageenans or alginates.

DESCRIPTION OF THE INVENTION

We have now discovered that it was possible to obtain gels, suitable as a support in deodorising or sanitising devices, by reacting, in the presence of a perfuming base, a liquid polymeric material with a cross-linking agent.

As it will become more apparent at the reading of the specific examples given hereinafter, the devices thus prepared offer several advantages over the prior art devices. In this respect, one can mention the fact that the support, once shaped, appears as a rigid dry and transparent material, which can contain a large proportion of perfume base, of up to 90% or more. This last feature is particularly important since the devices of the invention can accordingly be used in the form of discreet articles of small dimension, notwithstanding of good effectiveness. Thus, for example, these devices can find a utilisation to perfume closed small spaces such as cars, bathrooms, lavatories and so on. Owing to their transparency, they can be shaped in various and aesthetically appealing forms. What is more, their manufacture is very simple since, once homogenised, the polymer reaction mixture containing the perfuming base occurs in the form of a liquid which can be easily poured into moulds of the desired appropriate and varied form.

Lastly, solid articles can be shaped by reducing somewhat the proportion of the perfume base —e.g. to about 70% by weight relative to the weight of the polymer material —and by adding to the reaction mixture filling agents such as plaster, sawdust, metal powder or other similar materials.

We have discovered that certain functionalised polymers could be cross-linked in situ, in the presence of a perfume base, to form a gel which possessed the above-mentioned features.

The present invention provides a device for the perfuming, deodorising or sanitising of ambient air or closed spaces, which device comprises a gelified element resulting from the in situ cross-linking of a polymer, or a copolymer, in the presence of a perfuming, deodorising or sanitising base and/or a surfactant agent.

More particularly, the invention provides a device containing a gelified element resulting from the in situ cross-linking of a functionalised liquid polymer, or copolymer, and a cross-linking agent, in the presence of a perfuming, deodorising or sanitising base and/or a surfactant agent.

The invention also has as an object a process for perfuming a surfactant agent, which process is characterised in that a polymer, or copolymer, is cross-linked in situ in the presence of an active surfactant and a perfume base.

Preferred functionalised polymers according to the invention include the polymer materials miscible to the current perfume materials, which polymers possess one or several functional groups. Likewise, the cross-linking agent must possess one or more complementary functional groups. The mixture of these two elements gives, in the presence of a perfume base, a reaction which results in the formation of a three-dimensional network enclosing the perfume base.

The functional groups and the complementary functional groups may be respectively carboxylic acid, anhydride or acid chloride derived groups and amine or alcohol groups. Preferably, one can choose liquid polymers possessing functions derived from carboxylic acids, anhydrides or acid chloride and cross-linking agents having an amine or an alcohol fiction, but the reverse can also apply.

The functional groups on the polymer or the cross-linking agent may be mono-or poly-functional. To obtain a three-dimensional network, it is however necessary to have the presence of at least two functional groups per molecule of the liquid polymer and of the cross-linking agent alike.

By the terms "functionalised liquid polymer" it is deemed here to refer to a material which is liquid at room temperature and which possesses a viscosity of not more than 5000 poise at 25° C., preferably of about 250 to 1000 poise. As indicated above, both the liquid polymer material and the cross-linking agent must be soluble in the perfume base. Solubility can be achieved by straight solution in the perfume base or by adding an appropriate specific solvent. In practice, we have observed that by using large proportions of perfume base, such as those employed according to a preferred embodiments of the invention, such a complementary addition of solvent is not necessary.

The polymer material can be selected amongst the numerous polymers capable of functionalization. Preferred polymers are selected from the group of polyolefines, more particularly amongst polymers derived from mono- or di-olefines containing, prior to functionalization, at least one, and more preferably several, vinyl groups.

PREFERRED EMBODIMENTS OF THE INVENTION

According to a preferred embodiment of the invention, there are used polymers which are derivatives of butadiene, isoprene or chloroprene. More preferred is maleinised polybutadiene of MW 5000–20.000, or maleinised polyisoprene of MW 200,000–500.000. These are commercially available materials. Examples of these materials are provided in EP patent application N° 023 084, the disclosure of which is enclosed herein by reference. As an example, one can mention the product known under the name of "Lithene" |origin: Revertex Ltd|. Amongst the different qualities of available Lithene, good results have been obtained by using "Lithene N4-9000 10MA" |origin: Revertex Ltd|; 9000 stands for the molecular weight of polybutadiene before maleinisation, whilst 10MA indicates the degree of maleinisation —in this case 10 parts of maleic anhydride per 100 parts of polybutadiene (=about 9.1%) —.

The above-cited EP patent application gives also indications concerning the choice of cross-linking agents. The discriminating criterion for this selection is represented by the solubility of such an agent in the reaction medium, namely in the components of the perfume base. As suggested in the cited EP application, agents which satisfy such a criterion include dihydroxy polybutadiene. Ethoxylated primary amines are however preferred. Amongst the latter, more preferred are oleylamines possessing 2 moieties of ethylene oxide per molecule. Other cross-linking agents can be selected amongst the group of alkylpropyldiamines having an ethoxylated or propoxylated higher aliphatic chain (e.g. "Dicrodamet" ; origin: Croda Chemicals Ltd), diethanolamine or diethylenetriamine.

Equally useful have been found to be the cross-linking agents constituted by polyoxy- alkylenediamines. More particularly, the use of Jeffamine D-400, Jeffamine EDR-148 and Jeffamine D-2000 is very advantageous (Jeffamine is a registered trademark of Huntsman Corp.).

Also useful according to the invention are cocoamines having 5 ethylene oxide units per molecule. These are commercial products known under the name of "Crodamet" |origin: Croda Chemicals Ltd|.

The functionalised liquid polymer and the cross-linking agent are mixed in a molar ratio of between about 3:1 and 0.5:1, preferably of 1:1, based on the molar ratio of the functional groups which are present.

The gelified element according to the invention can also be obtained by mixing two polymers possessing complementary functionalities. Of course, the two polymers must be soluble in the perfuming or sanitising base. For example, it is possible to use a polybutadiene having a hydroxylic function such as HFPB (origin:Revertex Ltd) which gelifies when admixed with maleinised polybutadiene. Sometimes, the use of specific catalysts allows better control of the gel formation and, to this end, there are used tertiary amines (e.g.: DAMA 1010 ; origin: Albemarle SA). Mixtures of Hycar CTBN 1300 x21 (origin: B. F. Goodrich) and maleinised polybutadiene are also perfectly convenient.

According to a variant of the invention device, a copolymer is used as polymer, instead of a functionalised liquid polymer. Suitable copolymers include EMA, a copolymer of ethylene and maleic anhydride, a free flowing homogeneous powder.

As a perfume base there is used in the device of the invention any of the current compositions used in perfumery. These can be discreet chemicals; more often, however, they are more or less complex mixtures of volatile liquid ingredients of natural or synthetic origin. The nature of these ingredients can be found in specialised books of perfumery, e.g. in S. Arctander (Perfume and Flavor Chemicals, Montclair N.J., USA 1969).

As indicated above, one of the characterising elements of both the functionalised liquid polymer and the cross-linking agent, useful for the preparation of the invention's device, is their solubility in the perfuming, deodorising or sanitising base chosen. It is also understood that both the liquid polymer and the cross-linking agent can be dissolved in appropriate organic solvents before cross-linking. However, such an operation is superfluous in most of the cases, the active base, especially the perfume base, being sufficient to dissolve them and the use of a supplementary solvent being unnecessary.

Although special mention has been made hereinabove of the perfuming effect exerted by the invention device, the same principles apply to the manufacture of analogous devices for the diffusion of deodorising or sanitising vapours, the perfume base being then replaced by a deodorising composition, a bactericide, an insecticide, a repellent or even an attractant. By the term "sanitising", we refer here not only to those substances which can enhance the degree of acceptance of surrounding air by the observer, but also to those substances which can exert an attractant or repellent effect towards certain species of insects, for instance towards houseflies or mosquitoes, or else as bactericide.

One of the objects of the invention is therefore to provide a perfuming, deodorising or sanitising device containing a gelified element resulting from the in situ cross-linking between a functionalised liquid polymer, or a copolymer, and a cross-linking agent, in the presence of a perfuming, a deodorising or a sanitising base.

The invention is better illustrated by the following examples wherein the abbreviations have the meaning common in the art and the temperatures are indicated in degrees centigrade.

EXAMPLE 1

2.23 g of Lithene N4-9000 10MA and 10.28 g of a perfume base (Splash 115.032 BGE; origin: Firmenich SA, Geneva, Switzerland) were manually mixed in an appropriate vessel. 0.34 g of Crodamet 02 were then added under stirring. After about 10 min at room temperature, the resulting polymer oil gelled encapsulating the perfume base. Gel setting was complete in about half an hour.

EXAMPLE 2

2.56 g of Lithene N4-9000 10MA and 12.43 g of a perfume base (Splash 115.032 BGE; origin: Firmenich SA, Geneva, Switzerland) were manually mixed, whereupon 0.55 g of Crodamet C5 were added under stirring. After about 2 hours at room temperature, the oil had gelled into a non-wetting lump. Even after 24 h the product was not as rigid as that prepared in Example 1.

EXAMPLE 3

2.29 g of Lithene N4-9000 10MA and 14.95 g of a perfume base (Splash 115.032 BGE; origin: Firmenich SA, Geneva, Switzerland) were stirred by hand, whereupon 1.98 g of Crodamet 02 were added with stirring. After approximately 20 min at room temperature, the oil mixture had gelled. The product was fully cured after approximately 50 min. The resulting product was softer than that prepared according to Example 2 which contained 80% by weight of the perfume base.

EXAMPLE 4

1.44 g of Lithene N4-9000 10MA were mixed by hand in a beaker with 14.93 g of a perfume base (Splash 115.032

BGE; origin: Firmenich SA, Geneva, Switzerland), whereupon 0.22 g of Crodamet 02 were added under stirring. After 40 min, the mixture gels. The product was fully cured after approximately 3 h. The resulting product, which encapsulated 90% by weight of the perfume base, was softer than those obtained according to Examples 2 and 3, which contained 80 and 85% by weight of perfume base, respectively.

EXAMPLE 5

2.50 g of Lithene N4-9000 10MA were placed in a beaker and 11.60 g of a perfume base (Brissago 144.034; origin: Firmenich SA, Geneva, Switzerland) were added and stirred by hand, whereupon 0.4 g of Crodamet 02 were added under manual stirring. The resulting oily mixture was then poured into Barex type moulds. After 15 min at room temperature, the oil had gelled into a rubbery, non-wetting lump.

EXAMPLE 6–8

By proceeding as indicated in the previous example but replacing the perfume base Brissago with identical proportions of Centifoline 144.036, Citronia 144.037 and Tristan 431.756 (origin: Finnenich SA, Geneva, Switzerland) there were obtained perfuming gels of good quality with a gelling time of between 10 and 25 min.

EXAMPLE 9

2.54 g of Lithene N4-9000 10MA and 6.23 g of a perfume base (Terminator 109365B; origin: Firmenich SA, Geneva, Switzerland) were mixed by hand and 0.13 g of Crodamet 02 (ratio: Lithene/Crodarnet ca. 3: 1) were added thereto under stirring. The resulting oil gelled in 15 min at ambient temperature.

EXAMPLE 10

By proceeding as indicated in the previous example but using a molar ratio of Lithene/Crodamet of 5: 1 instead of 3: 1, there is obtained a sticky gel which lacked a certain degree of rigidity.

EXAMPLE 11

1.87 g of Lithene N4-9000 10MA were mixed with 5.69 g of a perfume base (Terminator 109365B; origin: Firmenich SA, Geneva, Switzerland), whereupon 0.57 g of Crodamet 02 were added thereto under manual stirring. After approximately 20 min at room temperature, the oil gelled.

EXAMPLE 12

Approximately 2 g of Lithene N4-9000 10MA were placed in a beaker and mixed with the required amount of a perfume base (Honeysuckle 150061; origin: Firmenich SA, Geneva, Switzerland) until complete solution. The cross-linking agents were pre-mixed and added under stirring to the perfume polymer base, then the mixture was poured into appropriate moulds and left to rest at room temperature until complete gel setting.

| % w/w Honeysuckle 150061 | 80.00 | 80.00 | 80.00 | 80.00 |
|---|---|---|---|---|
| % w/w Lithene N4-9000 10M-A | 17.14 | 17.49 | 17.85 | 18.24 |
| % w/w Jeffamine D-400 | 2.86 | 2.27 | 1.66 | 1.01 |
| % w/w Jeffamine EDR-148 | — | 0.24 | 0.49 | 0.75 |
| Gelling time (min) | 59 | 33 | 21 | 7 |

EXAMPLE 13

2.13 g of Lithene N4-9000 10MA were placed in a beaker and mixed with 9.94 g of a perfume base (Beach 68536; origin: Firmenich SA, Geneva, Switzerland). After complete solution, 0.35g of Jeffamine D-400 were added under stirring. 5 g of the mixture (which corresponds to 4 g of perfume base) were poured into a thermoformed pouch (28 ×46 mm) and let setting at room temperature. Left in the air, the gel lost 86% of the original weight of the perfume base in 43 days. Similar results were obtained by using Fresh Bouquet 433213 as perfume base (origin: Firmenich SA) used in the gel at a concentration of 80% by weight.

EXAMPLE 14

1.55 g of Lithene N4-9000 10MA were poured into an appropriate container and mixed with 3.82g of a perfume base (Lavande de Provence 150060 (origin: Firmenich SA, Geneva, Switzerland) until complete solution. In a separate beaker, 1.87 g of Hycar CTBN 1300 ×21 (origin: B.F. Goodrich) were dissolved in 4.13 g of the same perfume base, and 5.37 g of this solution were added to the previously obtained perfumed solution of the polymer. A dry and rigid gel formed rapidly at ambient temperature.

EXAMPLE 15

17.14 g of Lithene N4-9000 10MA were added to a mixture constituted by 40 g of a liquid surfactant and 40 g of orange terpenes and the mixture was stirred by hand until complete solution. 2.86 g of Jeffamine D-400 were added thereto under stirring. In less than 2 minutes at ambient temperature, the mass gelled.

The surfactant used was any of the following:

15.1 Marlipal 24/70*

15.2 Marlipal O13/70*

15.3 Lutensol ON70**

(*) origin: Hüls (**) origin: BASF

I claim:

1. An anhydrous gel element comprising the cross-linked reaction product of a polymer selected from the group consisting of a functionalized liquid polymer and a copolymer of ethylene and maleic anhydride, and a cross-linking agent having at least one complementary functional group, in the presence of a perfume component comprising a perfume base, a deodorizing base, a sanitising base, or a surfactant, wherein the functionalized liquid polymer is maleinised polybutadiene or maleinised polyisoprene, and the polymer is sufficiently cross-linked by the cross-linking agent in the presence of the perfume component to encapsulate a portion of the perfume component.

2. The anhydrous gel element according to claim 1 wherein the polymer and the cross-linking agent are soluble in the perfume component.

3. The anhydrous gel element according to claim 1 wherein the polymer is maleinised polybutadiene having a molecular weight of 5,000 to 20,000 or maleinised polyisoprene having a molecular weight of 200,000 to 500,000.

4. The anhydrous gel element according to claim 1 wherein the cross-linking agent is selected from the group consisting of dihydroxypolybutadiene, an ethoxylated primary amine, an alkylpropyldiamine having an ethoxylated higher aliphatic chain, an alkylpropyldiamine having a propoxylated higher aliphatic chain, diethanolamine, diethylenetriamine, a polyoxy-alkylenediamine, and a cocoamine having 5 ethylene oxide units.

5. The anhydrous gel element according to claim 4 wherein the ethoxylated primary amine is an oleylamine having 2 ethylene oxide units.

6. The anhydrous gel element according to claim 3 wherein the cross-linking agent is an oleylamine having two ethylene oxide units or a cocoamine having five ethylene oxide units per molecule.

7. The anhydrous gel element according to claim 3 wherein the polymer and the cross-linking agent are present in a molar proportion of about 1:1.

8. The anhydrous gel element according to claim 1 wherein the perfume component is present in an amount of about 70% to 90% by weight based on the weight of the polymer and the cross-linking agent.

9. A device comprising the anhydrous gel element of claim 1.

10. A method of perfuming, deodorizing or sanitising air, which comprises exposing the air to the anhydrous gel element in the device of claim 9.

11. An anhydrous gel element comprising the cross-linked reaction product of a hydroxylic polybutadiene and a maleinised polybutadiene, in the presence of a perfume component comprising a perfume base, a deodorizing base, a sanitising base, or a surfactant, wherein the maleinised polymer is sufficiently cross-linked to the hydroxylic polybutadiene in the presence of the perfume component to encapsulate a portion of the perfume component.

12. The anhydrous gel element of claim 11 further comprising a tertiary amine.

13. A method of perfuming a surfactant material, which comprises:

providing a mixture of a surfactant, a perfume base, a functionalized liquid polymer or a copolymer of ethylene and maleic anhydride, and a cross-linking agent, wherein the functionalized liquid polymer is selected from the group consisting of maleinised polybutadiene and maleinised polyisoprene, and the cross-linking agent has at least one complementary functional group; and cross-linking the polymer in the presence of the surfactant and the perfume base to produce an anhydrous gel element.

\* \* \* \* \*